United States Patent [19]

Morales et al.

[11] Patent Number: 5,480,640
[45] Date of Patent: Jan. 2, 1996

[54] ALPHA INTERFERON FOR TREATING PROSTATE CANCER

[75] Inventors: Alvaro Morales; James W. L. Wilson, both of Kingston, Canada

[73] Assignee: Schering Corporation, Kenilworth, N.J.

[21] Appl. No.: 432,742

[22] Filed: May 2, 1995

[51] Int. Cl.$^6$ .................................................. A61K 38/21
[52] U.S. Cl. ................................ 424/85.7; 530/351
[58] Field of Search ........................... 424/85.7; 530/351

[56] References Cited

U.S. PATENT DOCUMENTS

| | | | |
|---|---|---|---|
| 4,503,035 | 3/1985 | Pestka et al. | 424/85.7 |
| 4,846,782 | 7/1989 | Bonner | 424/85.7 |
| 4,997,645 | 3/1991 | Suzuki et al. | 424/85.7 |
| 5,256,410 | 10/1993 | Tanner et al. | 424/85.7 |

FOREIGN PATENT DOCUMENTS

WO92/19266  11/1992  WIPO.

OTHER PUBLICATIONS

Horoszewicz, et al., *J. Urology*, 142, 1173–1180 (1989).
van Haelst–Pisani, et al., *Cancer*, 70, (No. 9) 2310–2312 (1992).
van Moorselaar, et al., *The Prostate*, 18, 331–344 (1991).
Okutani, et al., *The Prostate*, 18, 73–80 (1991).
Ernstoff, et al., *Proc. Amer. Assoc. Cancer Res.*, 34, 204 (1993).
Chang, et al., *J. Interferon Res.*, 6, 713–715 (1986).
Sica, et al., *Urol. Res.*, 17, 111–115 (1989).
Dreicer, et al., *Urology*, 44, (No. 3) 377–380 (1994).
Pummer, et al., *Eur. Urol.*, 24, (Suppl. 2) 81–86 (1993).
Medenica, et al., *Cancer Drug Delivery*, 2, (No. 1) 53–76 (1985).
Jindal, et al., *Urol. Int.*, 52, 225–227 (1994).
Dell'Acqua, et al., *J. Tumor Marker Oncol.*, 5, (No. 3) 269 (1990).
Sica, et al., *Urol. Res.*, 22, 33–38 (1994).
Wickramasinghe et al, *J. Am. Acad. Dermatol.* 20: 71–74 (1989).
Grob et al, *Lancet*, 1, 878–879 (1988).

*Primary Examiner*—Howard E. Schain
*Attorney, Agent, or Firm*—Paul A. Thompson

[57] ABSTRACT

Described is a method for treating carcinoma of the prostate using recombinant human alpha interferon via intraprostatic or intralesional injection.

7 Claims, No Drawings

ALPHA INTERFERON FOR TREATING PROSTATE CANCER

This invention relates to a method for treating carcinoma of the prostate with recombinant human alpha interferon by administering the interferon directly into the prostate, i.e., via intraprostatic injection, or directly into the carcinoma lesion. i.e., intralesionally.

BACKGROUND OF THE INVENTION

Carcinoma of the prostate is a neoplasm most frequently occurring in males over 50 years of age and a leading cause of cancer deaths in men. Present treatment methods for localized prostatic carcinoma include radical prostatectomy or radiation therapy. Ten year cure rates for treatment of localized prostatic carcinoma up to 65% can be obtained using such methods. However, radical prostatectomy is a major surgical procedure and often results in impotence and urinary incontinence. Radiation therapy has a somewhat lower success rate than surgery, is generally well tolerated, but can also produce impotence, incontinence, cystitis and proctitis. Consequently there remains a need for a method or treating prostate cancer without such side effects.

SUMMARY OF THE INVENTION

The present invention fills the foregoing need by providing a method for treating human beings afflicted with prostate cancer.

More particularly, the present invention provides a method for treating carcinoma of the prostate comprising administering a therapeutically effective amount of alpha interferon by intraprostatic or intralesional injection.

Preferred for use in this invention is human interferon alfa-2b.

DETAILED DESCRIPTION

All references cited herein are hereby incorporated in their entirety by reference.

Human alpha interferon is a naturally occurring mixture of at least eleven components including those designated alpha-1 and alpha-2 interferon. Interferon alfa-2 can be produced in bacteria using recombinant techniques as disclosed in Rubenstein, *Biochem. Biophys. Acta*, 695, 5–16 (1982). In addition, interferon alfa-2 can be prepared by recombinant-DNA methods disclosed by Nagata, et al., *Nature*, 284, 316–320 (1980), European Patent No. 32, 134 and U.S. Pat. No. 4,289,690. Various alpha-2-interferon species are disclosed in U.S. Pat. No. 4,503,035.

Intralesional injection of alpha interferon, such as recombinant interferon alfa-2b, has been found to be effective for treatment of certain neoplasms, such as basal cell carcinoma, squamous cell carcinoma and urothelial tumors. See, U.S. Pat. No. 5,256,410 to Tanner, et al., Wickramasinghe. et al., *J. Am. Acad. Dermatol.*, 20, 71–74 (1989); Grob, et al., *Lancet*, 1, 878–879 (1988); and Kamidono, et al., *Kobe J. Med. Sci.*, 27, 207–212 (1981).

As used herein, the term "alpha interferon" means the family of highly homologous species-specific proteins that inhibit viral replication and cellular proliferation and modulate immune response, such as alpha-1 interferon (interferon alfa-1) or alpha-2 interferon (interferon alfa-2). Preferred alpha interferons include interferon alfa-2a, interferon alfa-2b, interferon alfa-2c, interferon alfa-n1 (a purified blend of natural alpha interferons), consensus alfa interferon, and interferon alfa-n3 (a mixture of natural alpha interferons). Alpha interferon for use in the present invention is available from a number of commercial sources, such as: Intron® A interferon alfa-2b from Schering Corporation, Kenilworth, N.J.; Roferon® A interferon alfa-2a from Hoffmann-LaRoche, Nutley, N.J.; Berofor® interferon alfa-2c from Boehringer-Ingelheim Pharmaceuticals, Inc., Ridgefield, Conn.; Sumiferon® interferon alfa-n1 from Sumitomo, Japan; Wellferon® interferon alfa-n1 from the Wellcome Foundation Ltd., London, Great Britain; consensus alfa interferon from Amgen, Inc., Newbury Park, Calif.; or Alferon® interferon alfa-n3 made by Interferon Sciences and available from the Purdue Frederick Co., Norwalk, Conn. Preferably the alpha interferon is human interferon alfa-2 (hIFN-$\alpha$2), and most preferably interferon alfa-2b.

A "therapeutically effective amount" of alpha interferon is herein defined as an amount which, when administered as described herein, produces favorable results.

"Favorable results" are herein defined as either a partial or complete response to treatment with alpha interferon. In determining such responses, all measurable lesions must be addressed with no new lesions or disease related symptoms detected.

"Complete response" is defined as the substantially complete disappearance of all evidence of disease.

"Partial response" is defined as a measurable regression of disease that amounts to less than complete response. Patients exhibiting a partial response include those patients with a decrease in serum prostate-specific antigen (PSA) levels of 50% or more.

For intralesional or intraprostatic administration, liquid injectable pharmaceutically acceptable compositions are used. Such compositions can be prepared by diluting freeze dried alpha interferon, such as hIFN-$\alpha$2, with sterile preservative free water to produce an isotonic solution containing the appropriate concentration of interferon. Other injectable compositions using saline, aqueous dextrose, glycerol, ethanol and the like, to thereby form a solution or suspension for injection can also be used. If desired, minor amounts of nontoxic auxiliary substances such as wetting or emulsifying agents, preservatives, pH buffering agents and the like (e.g. sodium acetate or sorbitan monolaurate), can be incorporated into the compositions. Actual methods of preparing such dosage forms are known, or will be apparent, to those skilled in the art, such as those methods described in, e.g. *Remington's Pharmaceutical Sciences* 18th Ed., A. Gennaro, ed., Mack Publishing Co. (Easton, Pa. 1990).

According to this invention, human beings are administered an effective amount of alpha-interferon for a period sufficient to treat prostatic carcinoma. The dosage range will typically be from about 0.1 to $20 \times 10^6$ International Units (I.U.) of alpha interferon per week for an initial period of about 5 weeks. In a typical 5 week dosage regimen for intralesional injection, human beings are administered progressively increasing dosages of about $1 \times 10^6$ I.U., $2 \times 10^6$ I.U., $3 \times 10^6$ I.U., $4 \times 10^6$ I.U., and $5 \times 10^6$ I.U. of hIFN-$\alpha$2 for weeks one to five, respectively. More preferably, a constant dosage of about $5 \times 10^6$ I.U. of hIFN-$\alpha$2 per week is administered for a period of 5 weeks. For intraprostatic injection larger doses may be required due to the larger area to be treated. For example, a preferred 5 week dosage regimen for intraprostatic injection comprises progressively increasing doses of $2 \times 10^6$ I.U., $4 \times 10^6$ I.U., $6 \times 10^6$ I.U., $8 \times 10^6$ I.U., and $10 \times 10^6$ I.U. of hIFN-$\alpha$2 for weeks one to five, respectively. Following completion of the inital 5 week regimen, patients are preferably administered a maintenance regimen of additional injections administered over the course of 6 to 12 months. A preferred maintenance regimen comprises intralesional or intraprostatic injections administered every two months for a period of one year. These doses and regimens should be considered only as guidelines. The attending clinician will determine, in his or her judgment, an appropriate dosage regimen, based on the patient's age and condition as well as the severity of the prostatic carcinoma.

The present invention can be illustrated by the following examples, but this invention is not to be construed as limited thereby.

EXAMPLES

Materials and Methods

Patients with histologically documented, clinically localized carcinoma of the prostate were treated according to the method of the present invention. All such patients had no more than 1 prostatic tumor of <3 cm in diameter, as determined by trans-rectal ultrasound of the prostate (TRUSP), in each lateral lobe of the prostate, and each tumor was surrounded by normal hyperplastic tissue and had an intact capsule.

Biopsies were performed on all patients 4–8 weeks prior to the start of treatment with alpha-interferon, and a bone scan and PSA determination were performed 1 week before treatment with interferon alfa-2b once per week for a period of 5 weeks. The dosages were $1\times10^6$ I.U., $2\times10^6$ I.U., $3\times10^6$ I.U., $4\times10^6$ I.U., and $5\times10^6$ I.U., for weeks one to five, respectively.

Intron® A interferon alfa-2b powder for injection manufactured by Schering Corporation was used. Vials containing Intron® A lyophilized powder equivalent to $5\times10^6$ IU were used. The lyophilized powder was stored at 2° to 8° C., and was reconstituted by addition of 1.0 mL of sterile or bacteriostatic water for injection U.S.P. The reconstituted drug was used directly or stored at 2° to 8° C. for up to one month. To prepare the appropriate dosage form the reconstituted solution was diluted as follows:

| Dosage (IU) | Volume of Reconstituted Solution | Volume of Water added |
| --- | --- | --- |
| $1 \times 10^6$ | 0.2 mL | 0.8 mL |
| $2 \times 10^6$ | 0.4 mL | 0.6 mL |
| $3 \times 10^6$ | 0.6 mL | 0.4 mL |
| $4 \times 10^6$ | 0.8 mL | 0.2 mL |
| $5 \times 10^6$ | 1.0 mL | 0 mL |

The injections were performed using TRUSP visualization to guide the injection needle. Preferably the needle was a 20 or 21 gauge spinal needle. Prior to treatment, the patients were administered an enema and one 400 mg tablet of norfloxacin, as recommended by Stamey, et al., *Monographs in Urology*, 9, 53–63 (1988). The injection needle was then guided, under TRUSP control, directly into the tumor nodule and surrounding areas and a specific quantity of alpha-interferon was injected such that substantially homogeneous distribution of the drug in the tumor was achieved. Patients were generally given local anesthesia to minimize discomfort.

Six weeks after completion of the treatment regimen, patients were examined by TRUSP and had TRUSP-guided biopsies of any suspicious lesions. Where no such lesions were detected, the area where tumor was previously documented was biopsied. Where biopsies are negative, additional follow-up biopsies were performed at weeks twelve, twenty, twenty eight and thirty six, post treatment. PSA levels were also monitored during treatment and follow-up.

Patient #1 was a 74 year old male with a histological diagnosis of Gleason IV/IV adenocarcinoma of the prostate. Following the second injection of Intron® A the nature of the prostatic nodule had become more diffuse and difficult to identify by ultrasound visualization. Following completion of the treatment protocol a significant reduction in the overall size of the gland was noted. Three separate sets of transrectal ultrasound directed biopsies of the prostate at three month intervals were all negative for tumor. The patient's PSA levels remained within normal limits during this period and were not elevated at the beginning of treatment. After 6 months there was a modest and temporary increase in the patient's PSA levels, which are now well within normal limits.

Patient #2 was a 70-year old man with histologically documented Gleason II–III adenocarcinoma of the prostate. The patient's PSA was elevated, however a laparoscopic lymph node dissection was negative. Following the third injection of Intron® A the lesion appeared to be more diffuse and harder to identify under ultrasound visualization. Following completion of the protocol, the first set of prostate biopsies showed the presence of adenocarcinoma of the same histological grade. The patient's serum PSA levels temporarily decreased, later returning to the pre-treatment levels. No significant change in prostate size was observed.

Patient #3 was a man with histologically documented stage B 1 disease with a moderate Gleason grading. Prior to treatment the patient's serum PSA was elevated at 7.6. The size of the tumor was significantly smaller following the third injection. Serum PSA levels showed a steady decrease and serum PSA was undetectable by completion of the protocol. There was no significant change in overall prostate size. Following completion of the protocol, the first transrectal ultrasound guided biopsies demonstrated no tumor in the area where the tumor was originally documented, however, adenocarcinoma of the prostate was documented at distant area. Subsequent prostate biopsies were all negative for tumor.

Treatment of these patients with Intron® A was well tolerated, and no significant localized side effects were seen.

Many modifications and variations of this invention will be apparent to those skilled in the art. The specific embodiments described herein are offered by way of example only, and the invention is not to be construed as limited thereby.

We claim:

1. A method for treating cancer of the prostate comprising administering a therapeutically effective amount of alpha interferon by intraprostatic or intralesional injection.

2. The method of claim 1 wherein the alpha interferon is administered by intraprostatic injection such that the whole prostate is infiltrated.

3. The method of claim 1 wherein the alpha interferon is administered by intralesional injection such that the entire lesion is infiltrated.

4. The method of claim 1 wherein the alpha interferon is selected from interferon alfa-2a, interferon alfa-2b, interferon alfa-2c, interferon alfa-n 1, consensus alfa interferon, and interferon alfa-n3.

5. The method of claim 4 wherein the alpha interferon is interferon alfa-2b.

6. The method of clam 5 wherein the interferon alfa-2b is administered once per week for a period of 5 weeks in progressively increasing dosages.

7. The method of claim 6 wherein the increasing dosages are $1\times10^6$, $2\times10^6$, $3\times10^6$, $4\times10^6$, and $5\times10^6$ I.U.

* * * * *